(12) United States Patent
Herrmann et al.

(10) Patent No.: US 8,662,748 B2
(45) Date of Patent: Mar. 4, 2014

(54) X-RAY DEVICE

(75) Inventors: Norbert Herrmann, Ebnath (DE); Andreas Limmer, Seybothenreuth (DE); Manfred Sechser, Neusorg (DE)

(73) Assignee: Siemens Aktiengesellschaft, München (DE)

( * ) Notice: Subject to any disclaimer, the term of this patent is extended or adjusted under 35 U.S.C. 154(b) by 126 days.

(21) Appl. No.: 13/108,788

(22) Filed: May 16, 2011

(65) Prior Publication Data

US 2012/0121071 A1     May 17, 2012

(30) Foreign Application Priority Data

May 18, 2010    (DE) .......................... 10 2010 020 780

(51) Int. Cl.
     *H05G 1/02*       (2006.01)
     *H05G 1/00*       (2006.01)

(52) U.S. Cl.
     USPC ............................ 378/194; 378/193; 378/204

(58) Field of Classification Search
     USPC .......... 378/101, 193, 194, 197, 198, 204, 210
     See application file for complete search history.

(56) References Cited

U.S. PATENT DOCUMENTS

| | | | |
|---|---|---|---|
| 5,450,466 A | 9/1995 | Kadowaki et al. | |
| 5,980,107 A * | 11/1999 | Kusch | 378/194 |
| 6,007,243 A | 12/1999 | Ergun et al. | |
| 6,789,941 B1 * | 9/2004 | Grady | 378/197 |
| 2007/0280426 A1 * | 12/2007 | Saffer | 378/198 |

FOREIGN PATENT DOCUMENTS

DE      196 30 888 A1      2/1998

OTHER PUBLICATIONS

German Office Action dated Feb. 28, 2011 for corresponding German Patent Application No. DE 10 2010 020 780.2-54 with English translation.

* cited by examiner

*Primary Examiner* — Anastasia Midkiff
(74) *Attorney, Agent, or Firm* — Lempia Summerfield Katz LLC

(57) ABSTRACT

An X-ray device including a C-arm movably guided on a mount is provided. A radiation source and a radiation detector are arranged on the C-arm. The radiation source and the radiation detector are connected to the C-arm by cables fed in from outside, the cables being arranged on a cable clamp that may be moved at least in segments along the C-arm.

20 Claims, 5 Drawing Sheets

X-RAY DEVICE

This application claims the benefit of DE 10 2010 020 780.2, filed May 18, 2010.

BACKGROUND

The present embodiments relate to an X-ray device including a C-arm that may be movably guided on a mount, a radiation source and a radiation detector arranged on the C-arm being connected to the C-arm by cables fed in from outside.

Mobile X-ray devices with C-arms are used, for example, in surgical operations or procedures. Due to the significant freedom of movement, the mobile X-ray devices may be easily moved by the staff away from and/or towards an examination object positioned on an operating table during the surgical procedure.

A radiation source and a radiation detector are disposed in opposing arrangement on free ends of the C-arm. The radiation source and the radiation detector are supplied by different supply lines or supply cables (e.g., depending on function) for the supply of power and for data transfer of the recorded X-ray detector signals. The supply cables may be grouped together in an external cable guide and guided to the C-arm. The cables may be connected in the form of cable loops at three attachment points, for example. Starting from an attachment to the C-arm, cables are mounted to an angle component and to a frame supporting the C-arm and the angle component. In this way, the cable loop between the C-arm and the angle component covers the orbital movement of the C-arm, and the cable loop between the angle component and the frame covers angulation movements, horizontal movements and lifting movements of the X-ray device.

Between these attachment points, cable length is retained so as not to restrict the freedom of movement of the X-ray device or the C-arm. The loop arranged on the C-arm may protrude into a sterile area (e.g., the inner radius of the C-arm) during certain movements of the C-arm. The disadvantage is also that an operator must ensure during an operation that when moving, the operator does not come into contact with the non-sterile cable. This may restrict the operator in freedom of movement.

SUMMARY AND DESCRIPTION

The present embodiments may obviate one or more of the drawbacks or limitations in the related art. For example, an X-ray device with a C-arm having an improved cable arrangement may be specified.

In one embodiment, an X-ray device with cables that are arranged on a cable clamp that may be moved along the C-arm, at least in segments, is provided.

The cable clamp may accommodate the cables that may be moved via at least one segment of the C-arm. The at least one segment of the C-arm may include a central segment. In this way, the disadvantages mentioned above (e.g., the risk of a cable such as the cable loop arranged on the C-arm projecting into the inner radius of the C-arm) are removed.

According to the present embodiments, the cable loop running between the C-arm and the angle component may be designed to be very short, thereby preventing projection of the cable loop into the inner radius of the C-arm. The entire orbital traveling distance of the C-arm may be provided by the mobility of the cable clamp. This is not solely a result of the length of the cable loop arranged on the C-arm (e.g., the length of the cable loop may be shortened according to the present embodiments) but in addition, via the possible traveling distance of the movable cable clamp along the C-arm.

The cable clamp may be carriage guided on a guide device. The carriage includes two functionally different segments: a movement segment that provides mobility, interacts with the guide device, and provides the arrangement of the carriage on the guide device; and an accommodating segment serving to accommodate the cable. The carriage is therefore guided via the guide device, such that the carriage is transported along with a movement of the C-arm. For example, the C-arm is in a normal or zero position in terms of an orbital mobility (e.g., an axis between the radiation source lying above and the corresponding radiation detector lying below forms a horizontal plumbline). The carriage is, for example, in a central position in relation to the circumference of the C-arm. In the event of an orbital movement of the C-arm, for example, in the clockwise direction, the carriage remains initially stationary despite movement of the C-arm, which runs almost under the carriage. The carriage starts to move when a drive segment, for example, positioned on the C-arm (e.g., at an end of the guide device) comes into contact with the carriage and transports the carriage according to the orbital movement of the C-arm. If the C-arm reverses, the carriage is initially stationary again until a second drive segment arranged, for example, on another end of the guide device comes into contact with the carriage and transports the carriage. If the C-arm does not move, the carriage does not move. The carriage may, therefore, not have a drive device.

In one embodiment, the guide device may have one or more rails or a guide channel for guiding the carriage. The carriage is connected in a stable arrangement with the one or more rails or the guide channel. An orbital length that defines the rail or the guide channel associated with the guide device defines the maximum traveling distance of the carriage. A rail or guide wire defining the traveling region of the carriage may, also be used. Any guide that may be attached to the C-arm and provides mobility of the carriage along the inner radius of the C-arm may be used.

In one embodiment, the carriage is on roller bearings or friction bearings. There are at least two different approaches, where a corresponding roller bearing or friction bearing may be provided on the C-arm (e.g., on the guide device) or on the carriage. For example, in the guide channel, corresponding roller or friction bearings, on which the carriage runs, may be arranged For example, the carriage may be moved along the carriage runs. For this purpose, for example, rolling elements (e.g., in the form of cylindrical rollers) may be provided in the guide channel. Alternatively, the carriage may have a segment on roller bearings or friction bearings, so that this includes, for example, at least one roller bearing or friction bearing rolling on at least one wall of the guide channel. In addition or alternatively, lubrication allowing friction movement on the guide channel and/or carriage-side roll surfaces may be used.

In one embodiment, the guide device may be configured as at least a toothed rack or toothed belt that is positioned at least in segments along the C-arm. The toothed rack or the toothed belt engages at least one toothed wheel driven by a motor arranged on the carriage. The carriage may drive itself according to this embodiment and may be moved irrespective of a movement of the C-arm. The traveling distance of the carriage is limited by the length of the toothed rack or the toothed belt arranged on the C-arm. A control device for driving the carriage thereby controls the direction of rotation and rotational speed of the motor enabling the toothed wheel arranged on the carriage to be driven. The motor may be controlled automatically or manually.

The cable clamp may be arranged inside a hollow segment of the C-arm. The cable clamp or the carriage may be accommodated within a C-arm profile configured, for example, using lightweight materials with one or more hollow internal chambers. The cable clamp barely projects into the inner radius of the C-arm, which is why the C-arm extends radially inwards by a small amount. The arm length provided by the internal chamber allows a sufficient traveling distance of the cable clamp.

The cable clamp may also be arranged externally on the inner radius of the C-arm. The C-arm may or may not be hollow. For a hollow C-arm, hollow segments may be used for a different purpose, so that no or insufficient room is available for the arrangement of the cable clamp. This type of arrangement of the cable clamp offers advantages by direct accessibility of the cable clamp, for example, for maintenance or repair purposes.

The cable clamp may be assigned a cable reserve. The cable reserve keeps sufficient cable length available for the movement of the cable clamp. The orbital mobility of the cable clamp is thus provided.

The cable reserve may be provided by a cable drum. The cable may be unrolled or rolled up depending on the traveling distance of the cable clamp by a shaft associated with the cable drum so that the cable length used for the current position or for movement of the cable clamp is constantly provided. The cable may not project into the inner radius of the C-arm, and the cable may not touch the floor. The cable drum is attached to the C-arm.

The cable reserve may also be arranged partly inside the C-arm. A cable allowing movement of the cable clamp along a traveling region is arranged accordingly inside the C-arm. When the cable clamp is moved, the cable is pulled over an opening of the C-arm and out of the C-arm profile and slides back into the C-arm when the cable is no longer used in the corresponding length. A sufficiently large accommodating space is provided for the cable within the C-arm profile.

The cable reserve may also be formed as a loop guided with the cable clamp. The loop is arranged closely adjacent in the radius of the C-arm or fastened to the arm, making it difficult for an operator to come into contact with the loop. The freedom of movement of the operator is therefore not limited, and contact between the cable and the floor is prevented.

The loop may be arranged on or in at least one supporting element connected directly or indirectly to the cable clamp. The supporting element (e.g., a conduit) serves to support or accommodate the loop, so that the loop is always mounted in a stable manner, is not dangling loosely and cannot come into contact with the floor in one embodiment.

The supporting element may be directly fastened to the cable clamp by suitable attachment (e.g., in the form of screws) so that the supporting element is moved with the cable clamp. The supporting element and the cable clamp may be joined by a weld joint or an adhesive joint, for example. In another embodiment, the supporting element may not be connected directly to the cable clamp but via a connection device (e.g., in the form of a junction plate or a stop fastened to the cable clamp). The connection device is connected between the cable clamp and the supporting element. Other types of connection between the supporting element and the connection device or between the connecting device and the cable clamp may be used.

DETAILED DESCRIPTION OF THE DRAWINGS

Figure 1:
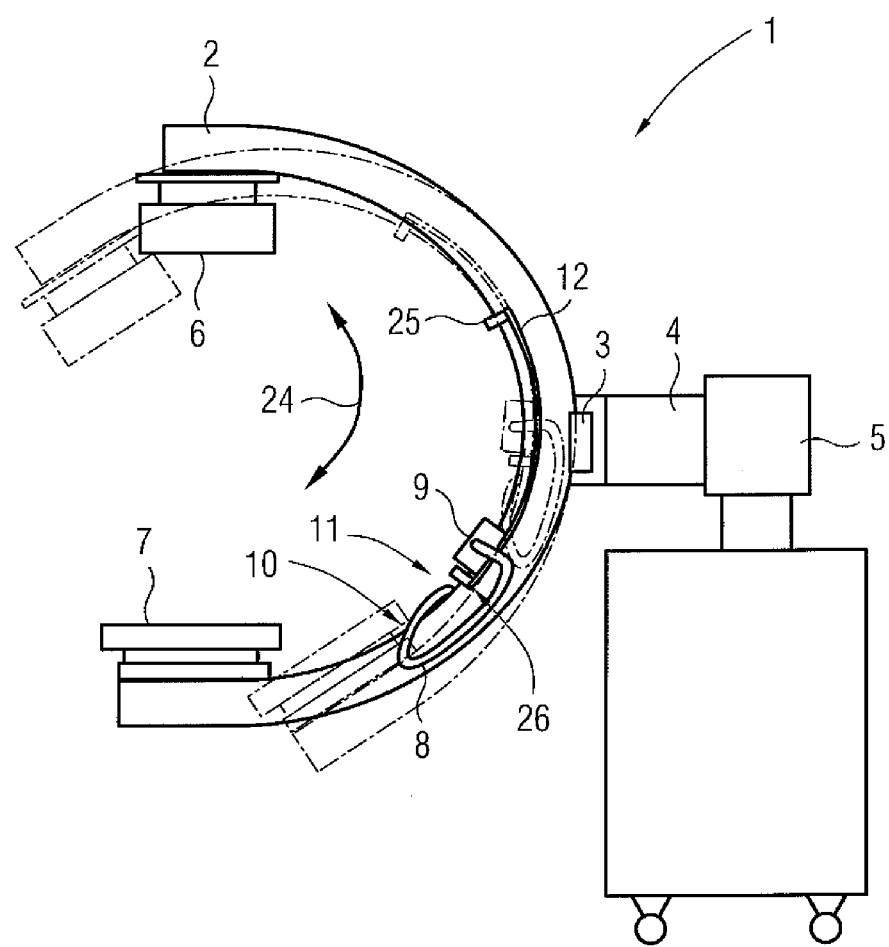
FIG. 1 shows one embodiment of an X-ray device.

FIG. 1 shows an X-ray device 1 with a C-arm 2. The C-arm 2 is connected using a mount 3, along which the C-arm 2 is movably guided in an orbital direction to an angle component 4 and a frame 5 of the X-ray device 1. The C-arm 2 may also be arranged on an industrial robot having, for example, six degrees of freedom. A radiation source 6 and a radiation detector 7 are disposed in opposing arrangement at ends of the C-arm 2. The radiation source 6 and the radiation detector 7 are connected to the C-arm 2 by cables fed in from outside. The cables are guided in a cable sheath 8. The cable sheath 8 may be configured as a zipper sheath to increase flexibility.

The cable sheath 8 is connected to a cable clamp configured as a carriage 9, for example and arranged on the outside (e.g., an outer surface) in the inner radius of the C-arm 2. The cable sheath 8 runs further as a loop 10 serving as cable reserve to the C-arm 2 until the cable sheath 8 opens into an opening 11 of the C-arm 2. The cable sheath 8 runs from the opening 11 to the radiation source 6 and to the radiation detector 7. An end of the cable sheath 8 is fastened by attachment points to the angle component 4 and to the frame 5 of the X-ray device 1.

The carriage 9 may be moved in segments along the C-arm 2. The carriage 9 may be moved along a defined traveling region by a guide device in the form of wires 12 running on the outside of the C-arm 2 (e.g., see double-headed arrow 24). Stops 25, 26 arranged on ends of the wires 12 transport the carriage 9 with the stops 25, 26 in an orbital direction. According to FIG. 1, the stop 26 is in contact with the carriage 9. Thus, a rotation of the C-arm 2 in a counter-clockwise direction causes the carriage 9 to move (e.g., see the broken line in FIG. 1). If the C-arm 2 moves in the clockwise direction, the carriage 9 remains unmoved until the stop 25 is in contact with the carriage 9 and transports the carriage 9 with the stop 25 accordingly.

The length of the cable sheath 8 forming the loop 10 may be insufficient to perform the entire traveling distance of the C-arm 2 in an orbital direction. This may be possible using the orbital movement of the carriage 9, which transports the cable sheath 8 with the carriage 9. The carriage 9 does not have a drive but is transported by the movement of the C-arm 2. One of the stops 25, 26 on the C-arm 2 engages the carriage 9 as described and pushes the carriage 9 along the wires 12. The carriage 9 is transported by the C-arm 2 when one of the stops 25, 26 (e.g., each of which may be arranged in a region of ends of the guide device or the wires 12) comes into contact with the carriage 9.

By the closely fitting (e.g., space-saving) arrangement of the cable sheath 8 on the C-arm 2 and the shortness of the cable sheath 8, the sheath does not protrude into the inner radius of the C-arm 2, come into contact with the floor or get in the way of an operator.

Figure 2:
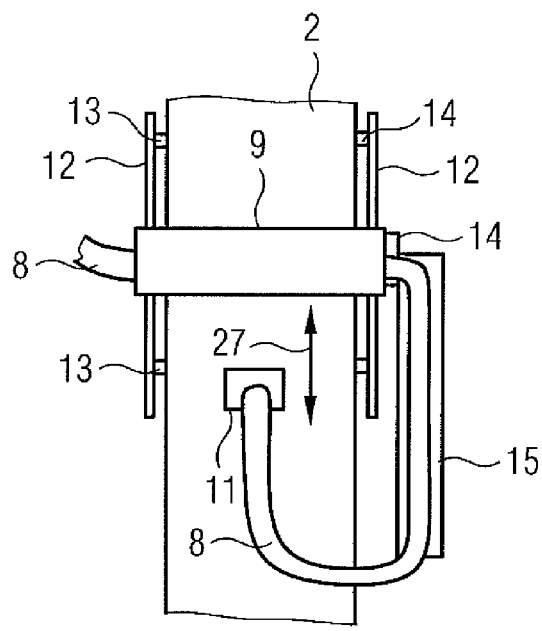
FIG. 2 shows a top view of a segment of a C-arm.

FIG. 2 shows a top view of a segment of the C-arm 2 or a different C-arm. The guide wires 12 are mounted on the outside of the C-arm 2 via suitable fastening segments, (e.g., clamps 13). The carriage 9, which accommodates part of the cable sheath 8, may be moved along the guide wires 12 and may therefore be moved via a route defined by the length of the guide wires 12 within the inner radius of the C-arm 2 (e.g., see double-headed arrow 27).

Figure 3:
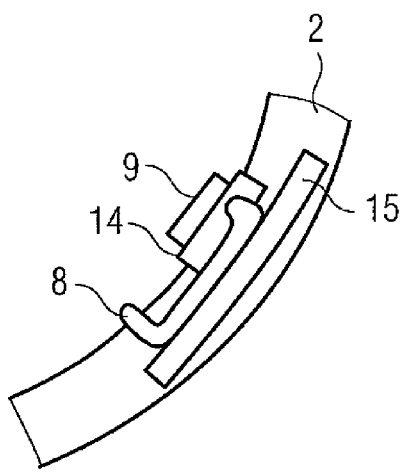
FIG. 3 shows a side view of a segment of a C-arm.

A supporting element in the form of a conduit 15, for example, is mounted to the carriage 9 using a junction plate 14 that supports the cable sheath 8 (e.g., see FIG. 3).

Figure 4:
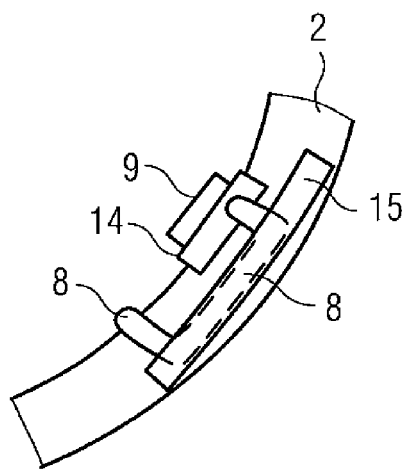
FIG. 4 shows a side view of a segment of a C-arm.

In one embodiment, the cable sheath 8 may be accommodated within the conduit 15 (e.g., see the broken lines in FIG. 4). The conduit 15 may be coupled in a movable manner to the carriage 9, so that the conduit 15 is transported with the carriage 9 when the carriage 9 moves.

FIGS. 5 to 8 relate to embodiments, in which the cable clamp (e.g., the carriage 9) is arranged inside a guide channel 16 (e.g., inside the C-arm 2) and may be moved within a hollow segment of the C-arm 2. This has the advantage that, as regards to the internal radius of the C-arm 2, the C-arm 2 extends radially inwards by a smaller amount as a result of the carriage 9. Within the carriage 9, a void 23 for accommodating the cable running in the C-arm 2 (e.g., essentially the supply cable of the radiation source 6 and the radiation detector 7) is provided.

Figure 5:
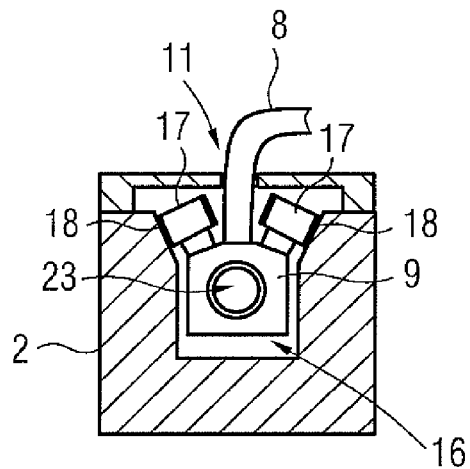
FIG. 5 shows a cross-section through a C-arm.

As shown in FIG. 5, roller bearings 17 may be arranged on a top side of the carriage 9. The roller bearings 17 roll on segments of the guide channel 16 configured as running surfaces 18, and in this way, enable a movement of the carriage 9 within the C-arm 2. In the C-arm 2, an orbital slit-like opening 18 is provided in segments corresponding to a traveling distance of the carriage 9. The cable sheath 8 is guided through the opening 18 outwards and further towards the angle component 4 (e.g., see FIG. 8, which shows a linear arrangement of the roller bearing 17 on the carriage 9, where the roller bearings 17 roll directly on inner walls of the slit-like opening 18). In one embodiment, a lubricant (e.g., in the form of grease) may be applied to all or some frictionally-active surfaces.

Figure 6:
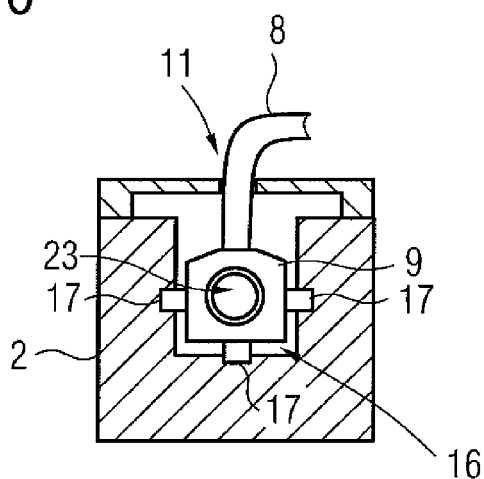
FIG. 6 shows a cross-section through a C-arm.

FIG. 6 shows one embodiment where the roller bearings 17 are positioned on walls of the guide channel 16.

Instead of or in addition to the roller bearings 17, friction bearings or friction segments (e.g., of Teflon) (not shown) may be used.

Figure 7:
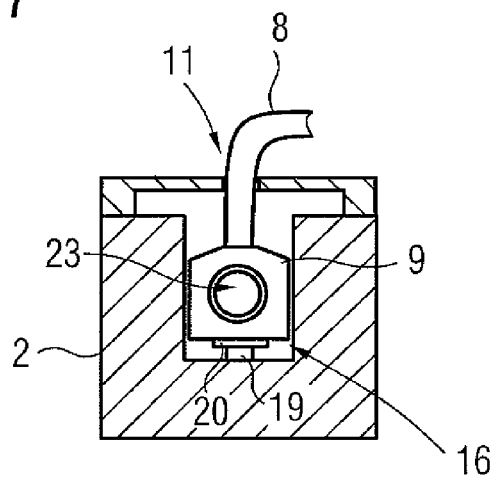
FIG. 7 shows a cross-section through a C-arm.
Figure 8:
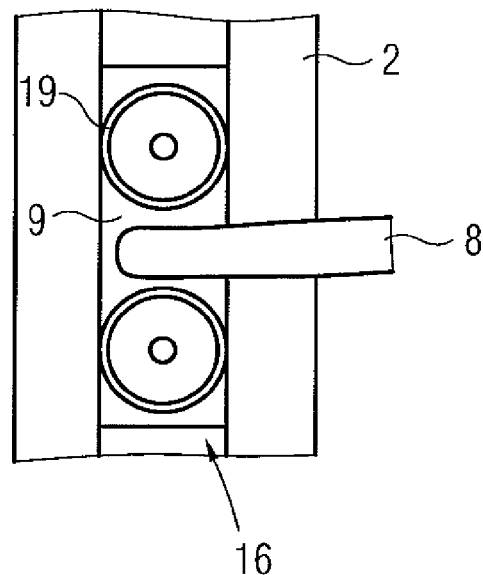
FIG. 8 shows a top view of a segment of a C-arm.
Figure 10:
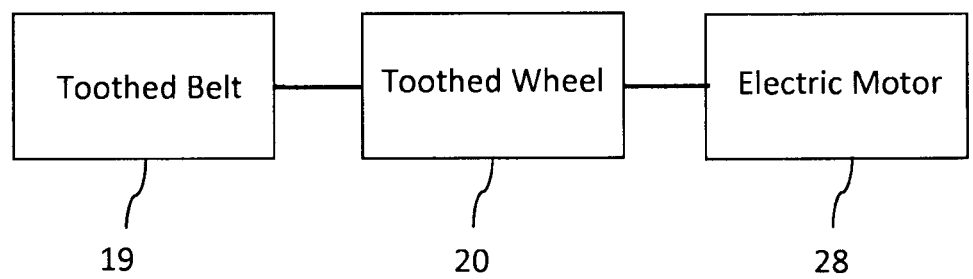
FIG. 10 shows one embodiment including a toothed wheel, an electric motor, and a toothed belt.

The embodiment according to FIG. 7 shows a toothed belt 19 arranged on the inside of the guide channel 16. A toothed wheel 20 configured on the carriage 9 may be driven, for example, via an electric motor 28 and engages with the toothed belt 19 (see FIG. 10). The operation of the motor (e.g., essentially the rotational speed and direction of the torque) may be controlled by a suitable control device. The carriage 9 may have a drive and may not be transported by the C-arm 2 or on a stop positioned on the C-arm.

Figure 9:
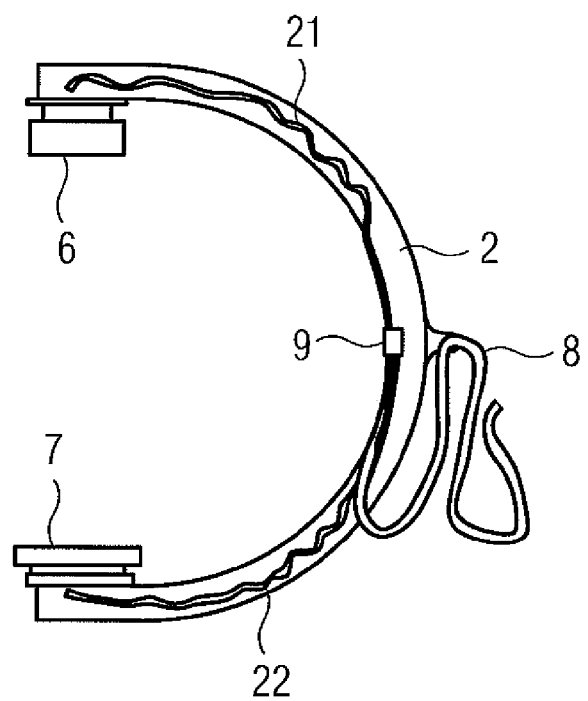
FIG. 9 shows a longitudinal section through a C-arm.

FIG. 9 shows a further possibility for keeping cable in reserve for the carriage 9. A cable reserve may be provided directly within the C-arm 2 (e.g., the cable sheath 8 coming from the angle component 4 is guided directly into the interior of the C-arm 2). The cables 21, 22 on the carriage 9 leading to the radiation source 6 or the radiation detector 7 open out into the cable sheath 8 and are accommodated by this.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An X-ray device comprising:
   a mount;
   a C-arm that is operable to be guided in a movable manner on the mount;
   a radiation source and a radiation detector arranged on the C-arm, the radiation source and the radiation detector being connected to the C-arm by cables that are externally supplied; and
   a cable clamp supported by the C-arm, the cable clamp being movable along the C-arm,
   wherein the cables are arranged on the cable clamp.

2. The X-ray device as claimed in claim 1, wherein the cable clamp is a carriage guided on a guide device.

3. The X-ray device as claimed in claim 2, wherein the guide device comprises one or more rails or a guide channel for guiding the carriage.

4. The X-ray device as claimed in claim 2, wherein the carriage is mounted on a roller bearing or friction bearing.

5. The X-ray device as claimed in claim 2, wherein the guide device comprises a toothed rack or a toothed belt configured at least in segments along the C-arm, and
   wherein a toothed wheel arranged on the carriage and drivable by a motor engages the toothed rack or the toothed belt.

6. The X-ray device as claimed in claim 1, wherein the cable clamp is arranged inside a hollow segment of the C-arm.

7. The X-ray device as claimed in claim 1, wherein the cable clamp is arranged on an outer surface of the inner radius of the C-arm.

8. The X-ray device as claimed in claim 1, wherein a cable reserve is assigned to the cable clamp, the cable reserve holding sufficient cable length for the movement of the cable clamp.

9. The X-ray device as claimed in claim 8, wherein the cable reserve is formed by a cable drum.

10. The X-ray device as claimed in claim 8, wherein the cable reserve is arranged partly within the C-arm.

11. The X-ray device as claimed in claim 8, wherein the cable reserve is formed as a loop guided by the cable clamp.

12. The X-ray device as claimed in claim 11, wherein the loop is arranged on or in a supporting element connected directly or indirectly to the cable clamp.

13. The X-ray device as claimed in claim 12, wherein the supporting element is a conduit.

14. The X-ray device as claimed in claim 2, wherein the cable clamp is arranged inside a hollow segment of the C-arm.

15. The X-ray device as claimed in claim 3, wherein the cable clamp is arranged inside a hollow segment of the C-arm.

16. The X-ray device as claimed in claim 4, wherein the cable clamp is arranged inside a hollow segment of the C-arm.

17. The X-ray device as claimed in claim 5, wherein the cable clamp is arranged inside a hollow segment of the C-arm.

18. The X-ray device as claimed in claim 2, wherein a cable reserve is assigned to the cable clamp, the cable reserve holding sufficient cable length for the movement of the cable clamp.

19. The X-ray device as claimed in claim 6, wherein a cable reserve is assigned to the cable clamp, the cable reserve holding sufficient cable length for the movement of the cable clamp.

20. The X-ray device as claimed in claim 7, wherein a cable reserve is assigned to the cable clamp, the cable reserve holding sufficient cable length for the movement of the cable clamp.

* * * * *